United States Patent [19]
Beavers

[11] Patent Number: 5,912,364
[45] Date of Patent: Jun. 15, 1999

[54] PROCESS FOR THE PREPARATION OF 3-METHYLTETRAHYDROFURAN

[75] Inventor: William Anthony Beavers, Longview, Tex.

[73] Assignee: Eastman Chemical Company, Kingsport, Tenn.

[21] Appl. No.: 08/944,653

[22] Filed: Oct. 6, 1997

Related U.S. Application Data

[60] Provisional application No. 60/028,978, Oct. 21, 1996.
[51] Int. Cl.⁶ .................................................. C07D 307/06
[52] U.S. Cl. ........................................... 549/429; 549/497
[58] Field of Search ..................................... 549/429, 506, 549/497

[56] References Cited

U.S. PATENT DOCUMENTS

| | | | |
|---|---|---|---|
| 3,859,369 | 1/1975 | Copelin | 260/635 |
| 3,932,468 | 1/1976 | Kurkov | 260/346.1 |
| 3,933,861 | 1/1976 | Kurkov | 549/506 |
| 4,323,509 | 4/1982 | Milner | 549/506 |
| 4,376,208 | 3/1983 | Vietti | 549/478 |
| 4,479,017 | 10/1984 | Ayusawa et al. | 568/613 |
| 4,590,312 | 5/1986 | Ernst | 568/861 |
| 4,742,178 | 5/1988 | Nelson et al. | 568/454 |
| 4,774,362 | 9/1988 | Devon et al. | 568/454 |
| 4,845,306 | 7/1989 | Puckette | 568/454 |
| 4,871,878 | 10/1989 | Puckette et al. | 568/454 |
| 4,879,420 | 11/1989 | Ernst | 568/617 |
| 4,960,949 | 10/1990 | Devon et al. | 568/454 |
| 5,536,854 | 7/1996 | Weyer et al. | 549/508 |

FOREIGN PATENT DOCUMENTS

| | | |
|---|---|---|
| 0 75 952 | 4/1983 | European Pat. Off. . |
| 0 727 422 | 8/1996 | European Pat. Off. . |
| 0 747 373 | 12/1996 | European Pat. Off. . |
| 3224033 | 1/1983 | Germany . |
| 79-135714 | 10/1979 | Japan . |
| 61-40227 | 2/1986 | Japan . |
| 8-217708 | 8/1996 | Japan . |
| 8-217770 | 8/1996 | Japan . |
| 8-217771 | 8/1996 | Japan . |
| 8-291158 | 11/1996 | Japan . |
| 77-68106 | 6/1997 | Japan . |

OTHER PUBLICATIONS

A Polo et al., Organometallics, 11, 3525 (1992).
Heterocycles, vol. 116, 1992; Abstract 128539p: V. Schiavo et al., Bull. Soc. Chim. Fr., 704 (1991).
F. Notheisz et al., J. Catal, 71, 331 (1981).
U. Gennari et al., Appl. Catal., 11, 341 (1984).
S. Teratini, Chem. Lett., 807 (1980).
R. Conner et al., J. Amer. Chem. Soc., 54, 4678 (1932).
H. Pines et al., J. Amer. Chem. Soc., 77, 5099 (1955).
A. R. Pinder, Synthesis, 425 (1980).

*Primary Examiner*—Amelia Owens
*Attorney, Agent, or Firm*—Michael J. Blake; Harry J. Gwinnell

[57] ABSTRACT

Disclosed is a process for the preparation of 3-methyltetrahydrofuran (3-MeTHF) which comprises contacting 3-formyltetrahydrofuran with hydrogen in the presence of a catalyst system comprising a Group VIII noble metal or rhenium and a strong acid under hydrogenolysis conditions of temperature and pressure to produce 3-MeTHF. The 3-MeTHF produced in accordance with the present invention is useful as an industrial solvent and, more importantly, as a monomer in the manufacture of polymers such as elastomers.

8 Claims, No Drawings

PROCESS FOR THE PREPARATION OF 3-METHYLTETRAHYDROFURAN

This application claims the benefit of U.S. provisional application Ser. No. 60/028,978, filed Oct. 21, 1996.

This invention pertains to a process for the preparation of 3-methyltetrahydrofuran (3-MeTHF) from 3-formyltetrahydrofuran (3-formylTHF). More specifically, this invention pertains to a process wherein 3-formylTHF is contacted with hydrogen in the presence of a particular catalyst system to convert the 3-formylTHF to 3-MeTHF. The 3-MeTHF produced in accordance with the present invention is useful as an industrial solvent and, more importantly, as a monomer in the manufacture of polymers such as elastomers.

3-MeTHF has been produced in commercial quantities by the high pressure hydrogenation of citraconic anhydride and some of its derivatives according to the procedures disclosed in U.S. Pat. No. 5,536,854 and Published Japanese Patent Application (Kokai) 08-217,771. Since citraconic acid is formed from citric acid or, more economically, as a minor by-product, during maleic anhydride production, these routes to 3-MeTHF are expensive and use a starting material which is not plentiful.

Processes for the production of 3-MeTHF based on less expensive precursors and precursors independent of the production of other materials have been developed. Thus, U.S. Pat. No. 3,932,468, describes a process for isomerizing isoprene monoepoxide into 4-methyl-2,3-di-hydrofuran using a nickel and hydrohalic acid catalyst. Although the hydrogenation of 4-methyl-2,3-dihydrofuran into 3-MeTHF is relatively simple, the synthesis of the starting material, isoprene monoepoxide, is not. For example, the preparation of isoprene monoepoxide would require the use of classical (and expensive) epoxide manufacturing techniques such as the use of halohydrins or co-oxidation with aldehydes. Japanese Published Patent Application (Kokai) JP 08-291,158 describes another method for preparing 3-MeTHF in which propylene is converted into 2-methylsuccinate esters by a double oxidative carbonylation in the presence of an alcohol. Although the reductive cyclization of the 2-methylsuccinate esters to 3-methyltetrahydrofuran is facile, the double oxidative carbonylation reaction usually gives limited yields of the dicarbonylated products and requires expensive, reactive solvents to keep the reagents anhydrous.

Another method for the synthesis of 3-MeTHF is disclosed in U.S. Pat. No. 3,859,369 and comprises the hydroformylation of 2-buten-1,4-diol into 2-methyl-1,4-butanediol which is converted to 3-MeTHF by acid catalysis. U.S. Pat. Nos. 4,590,312 and 4,879,420 describe the conversion of 4-hydroxybutyraldehyde and its immediate precursor, 2-buten-1,4-diol, into 3-MeTHF by reductive alkylation with formaldehyde followed by acid catalyzed cyclization. In each case, the products were mixtures of 3-MeTHF and tetrahydrofuran. This situation occurred in the hydroformylation process because isomerization accompanied the hydroformylation, limiting the yield of 3-MeTHF by forming a tetrahydrofuran precursor. In the reductive alkylation processes, the intermediate products as well as the starting materials could form alcohols by hydrogenation. Only those hydrogenations occurring after an initial aldol condensation of the reactants with formaldehyde could form 3-MeTHF. All other hydrogenations gave tetrahydrofuran or other byproducts.

Yet another method for the preparation of 3-MeTHF is disclosed in Published European Patent Application EP 727 422 and involves the hydrocyanation of methacrylate esters. A series of hydrolyses and esterifications forms a diester which may be reductively cyclized to 3-MeTHF using an acidic, copper chromite catalyst. In this case, not only were the starting materials expensive (although not as expensive as the citraconic anhydride derivatives), but the synthesis required four steps. Japanese Published Patent Application (Kokai) JP 08-217,708 describes a process for producing 3-MeTHF by the hydroformylation of methacrylate esters to form mixtures of the α-formylisobutyrate and the β-formylisobutyrate esters using synthesis gas. Japanese Published Patent Application (Kokai) JP 08-217,770 discloses a similar hydroformylation using methyl formate as the C-1 source. In both of these hydroformylation processes, hydrogenation of the resulting β-formylisobutyrate ester over a copper chromite catalyst gave 3-MeTHF. One further hydroformylation route reported in Published European Patent Application Publication EP 747,373 consists of (1) the hydroformylation of isobutenyl alcohol (2-methyl-2-propen-1-ol) to form 4-hydroxy-3-methylbutyraldehyde which (2) was readily hydrogenated with nickel catalysts to 2-methyl-1,4-butanediol and which (3) was cyclized to 3-MeTHF by acid catalysis.

U.S. Pat. No. 4,376,208 discloses the hydroformylation of 2,5-dihydrofuran employing a catalyst system comprising a rhodium-triarylphosphine complex in the presence of a tertiary amine cocatalyst. A. Polo, et al., *Organometallics*, 11, 3525 (1992), also disclose the hydroformylation of dihydrofurans and teach that the most effective catalysts are rhodium catalysts promoted with trialkyl phosphites. In each of these cases, the catalyst system caused the yield of the 3-formylTHF to depend critically upon the reaction conditions. One reason for this is that an integral component of the catalyst system was a basic amine which, in addition to the hydroformylation, promoted the aldol condensation of the formyl-reaction product. Therefore, even under conditions in which the initial yields of the 3-formylTHF may be high, the isolated yields are not.

In the prior art pertaining to the hydrogenolysis of furan derivatives, V. Schiavo, et al., *Bull. Soc. Chim. Fr.*, 704 (1991), report the hydrogenation and hydrogenolysis of furan derivatives to tetrahydrofurans, acyclic ketones, and acyclic alcohols over copper, nickel, and several Group VIII metal-based catalysts. The hydrogenolysis reactions were promoted by acidic promoters, high temperatures and high hydrogen pressures. Platinum and ruthenium were particularly good hydrogenolysis catalysts and hydrogenolysis apparently was easier with furans than with tetrahydrofuran derivatives. F. Notheisz, et al., *J. Catal*, 71, 331 (1981) describe the hydrogenolysis of oxacycloalkanes over platinum, palladium, and nickel catalysts. They reported that hydrogenolysis of the tetrahydrofurans occurred at the most accessible carbon, oxygen bond with all three metals capable of catalyzing hydrogenolysis at 60 to 300° C. U. Gennari, et al., Appl. Catal., 11, 341 (1984), report further the decarbonylation of the initially-produced, tetrahydrofuran hydrogenolysis intermediates as well as the complete deoxygenation to hydrocarbons even at temperatures as low as 100° C.

In contrast to the hydrogenolysis of furans and tetrahydrofurans, other ethers and alcohols undergo hydrogenolysis with varying degrees of difficulty. For example, Published Japanese Patent Application (Kokai) JP 79-135,714 discloses the Lewis acid-promoted hydrogenolysis of gem dialkoxy hydrocarbons catalyzed by supported rhodium and palladium catalysts under mild conditions producing ether products. Cleavage of the monoethers is much more difficult as shown by German Offenlegungsschrift DE 3,224,033 which discloses the hydrogenolysis of both geminal and vicinal ethers using palladium catalysts. The product consists almost exclusively of materials from the cleavage at the geminal position with only small contributions from materials coming from cleavage at all other ether positions. Nevertheless, such ether cleavages are possible at harsher conditions [European Published Patent Application Publication EP 75,952] using a supported ruthenium catalyst to achieve hydrogenolysis at each ether and hydroxyl position to produce an array of products from diethylene glycol. Comparing catalyst efficiencies in this hydrogenolysis, S. Teratini, Chem. Lett., 807 (1980), showed that palladium preferred to cleave C—O bonds (alcohols and ethers) compared with platinum which preferred to cleave C=O bonds.

The cleavage of alcohols is easier although by no means facile. Thus, Japanese Published Patent Application (Kokai) JP 61 40,227 describes the use of palladium and alumina catalysts in the hydrogenolysis of alcohols containing aromatic rings to produce the corresponding hydrocarbons while keeping the aromatic rings intact. Japanese Published Patent Application (Kokai) JP 77-68,106 discloses the hydrogenolysis of alcohols into the corresponding hydrocarbons using palladium on activated carbon promoted with phosphotungstic acid. R. Conner, et al., *J. Amer. Chem. Soc.*, 54, 4678 (1932) describes the relative ease of hydrogenolysis of one of the alcohol groups in 1,3-diols compared with 1,2-, 1,4-, or other diols. However, H. Pines, et al., *J. Amer. Chem. Soc.*, 77, 5099 (1955) report that nickel supported kieselguhr catalyzes the hydrogenolysis of primary alcohols to the corresponding hydrocarbons containing one less carbon atom unless the catalyst is selectively poisoned with sulfur compounds.

Another method to accomplish the hydrogenolyses of both ethers and alcohols is to convert them into their corresponding alkyl halides under the reaction conditions. The conversion of the alkyl halides into the corresponding hydrocarbon is not difficult as is disclosed by A. R. Pinder, Synthesis, 425 (1980), using platinum and palladium catalysts. One possible, significant disadvantage to this route may be the adverse (poisoning) effect the halides may have on the hydrogenation catalysts, requiring the use of additional catalyst.

The present invention is based on the discovery that 3-formylTHF can be converted to 3-MeTHF by means of a particular catalyst system comprising a Group VIII noble metal or rhenium and a strong acid. Thus, the process of this invention provides for the preparation of a 3-MeTHF by contacting 3-formylTHF with hydrogen in the presence of a catalyst system comprising a Group VIII noble metal and a strong acid under hydrogenolysis conditions of temperature and pressure to produce 3-MeTHF.

The 3-formylTHF used in the process may be obtained by contacting 2,5-dihydrofuran (2,5-DHF) with synthesis gas comprising carbon monoxide and hydrogen in the presence of a rhodium-phosphorus catalyst system according to known hydroformylation procedures. The rhodium component of the catalyst system can be provided by any one of various rhodium compounds soluble in the organic reaction medium in which the hydroformylation is carried out. Examples of such soluble rhodium compounds include tris(triphenylphosphine)rhodium chloride, tris(triphenylphosphine)rhodium bromide, tris(triphenylphosphine)rhodium iodide, tris(triphenylphosphine)rhodium fluoride, rhodium 2-ethylhexanoate dimer, rhodium acetate dimer, rhodium propionate dimer, rhodium butyrate dimer, rhodium valerate dimers, rhodium carbonate, rhodium octanoate dimer, dodecacarbonyltetrarhodium, rhodium(III) 2,4-pentanedionate, rhodium(I) dicarbonyl acetonylacetonate, tris(triphenylphosphine)rhodium carbonyl hydride [(Ph3P:)3Rh(CO)—H], and cationic rhodium complexes such as rhodium(cyclooctadiene)bis(tribenzylphosphine) tetraflouroborate and rhodium (norbornadiene)bis (triphenylphosphine) hexaflourophosphate.

The activity and selectivity of the catalyst system usually is relatively insensitive to the source of the rhodium. The concentration of rhodium [Rh] in the catalyst solution may be in the range of about 0.1 to 100,000 ppm although very low concentrations of rhodium are not commercially desirable since reaction rates will be unacceptably low. The upper limit on the rhodium concentration is not critical and is dictated principally by the high cost of rhodium. Thus, the concentration of rhodium [Rh] in the catalyst solution preferably is in the range of 10 to 10,000 and, most preferably, 100 to 5000 ppm.

Tertiary (trisubstituted) phosphine and phosphite compounds may be employed as the organophosphorus component of the catalyst system. Examples of such phosphines and phosphites include tributylphosphine, tributylphosphite, butyldiphenylphosphine, butyldiphenylphosphite, dibutylphenylphosphite, tribenzylphosphine, tribenzylphosphite, tricyclohexylphosphine, tricyclohexylphosphite, 1,2-bis(diphenylphosphino)ethane, 1,3-bis(diphenylphosphino)propane, 1,4-butanebis (dibenzylphosphite), 2,2'-bis(diphenylphosphinomethyl)-1, 1'-biphenyl, and 1,2-bis(diphenylphosphinomethyl)benzene. Additional examples of tertiary phosphines are disclosed in U.S. Pat. No. 4,845,306, 4,742,178, 4,774,362, 4,871,878 and 4,960,949. Typical phosphine and phosphite ligands may be represented by the general formulas

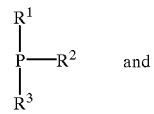
(I)

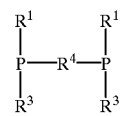
(II)

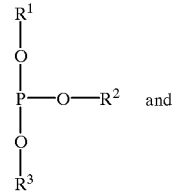
(III)

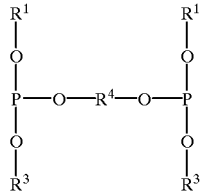
(IV)

wherein $R^1$, $R^2$ and $R^3$ are the same or different and each is hydrocarbyl containing up to about 12 carbon atoms and $R^4$ is a divalent hydrocarbylene group which links the 2 phosphorus atoms through a chain of 2 to 8 carbon atoms.

Examples of the hydrocarbyl groups which $R^1$, $R^2$ and $R^3$ may represent include alkyl including aryl-substituted alkyl such as benzyl, cycloalkyl such as cyclohexyl, and aryl such as phenyl and phenyl substituted with one or more alkyl groups. Alkylene such as ethylene, trimethylene and hexamethylene, cycloalkylene such as cyclohexylene, and phenylene, naphthylene and biphenylene are examples of the hydrocarbylene groups which $R^4$ may represent.

The organophosphorus component of the catalyst system preferably is a trisubstituted mono-phosphine compound such as those having formula (I) above. Triphenylphosphine, tricyclohexylphosphine, and, tribenzylphosphine are the most preferred organophosphorus compounds. The ratio of moles of organophosphorus compound to gram atoms of rhodium present in the catalyst system typically is about 2:1 to 10,000:1 with ratios in the range of 2.5:1 to 1000:1 being preferred and 3:1 to 100:1 being most preferred.

The hydroformylation of 2,5-DHF may be carried out at a temperature in the range of about 40 to 180° C. However, to minimize isomerization of the 2,5-DHF reactant to 2,3-dihydrofuran (2,3-DHF), the hydroformylation normally will be performed at a temperature in the range of about 50 to 80° C. Isomerization of the 2,5-DHF reactant to 2,3-DHF leads to the formation of a mixture of 2- and 3-formylTHF. Coproduction of these isomers presents no problem in separation, but it does limit the upper yield of the desired 3-formylTHF to about 30% because 2,3-DHF produces 2- and 3-formylTHF in 3:1 ratios.

The total pressure used in the hydroformylation may be in the range of about 0.01 to 35 mPa (about 1.5 to 5000 psig) with total pressures in the range of about 0.35 to 7 mPa (about 50 to 1000 psig) being preferred. The mole ratio of carbon monoxide to hydrogen in the synthesis gas may be about 3:1 to 0.3:1 with mole ratios of about 2:1 to 0.5:1 be more common and preferred. The hydroformylation may be carried out in the presence of an extraneous, inert, organic solvent. Examples of such solvents include aliphatic hydrocarbons containing 3 to 20 carbon atoms, aromatic hydrocarbons containing 6 to 18 carbon atoms, ethers including glycol ethers containing 2 to 20 carbon atoms, and alcohols containing up to 20 carbon atoms. An inert, water-immiscible, hydroformylation solvent selected from aliphatic and aromatic hydrocarbons, ethers and alkanols containing 8 to 20 carbon atoms may be used advantageously in conjunction with a product extraction using water as the extractant to enhance product and catalyst recovery.

The 3-formylTHF product may be recovered from the hydroformylation mixture by distillation, gas sparging, gas stripping or product flash procedures using a temperature below 70° C. The 3-formylTHF product preferably is isolated from the reaction mixture, especially from the catalyst components, by extracting the product into deoxygenated water. After the crude product has been separated from the catalyst system by one of these methods, it may be subjected to fractional distillation to separate a minor amount of 2-formylTHF by-product from the 3-formylTHF. The extraction of the product into deoxygenated water solves a number of technical difficulties and provides a suitable feedstock for the hydrogenolysis process of the invention without further purification.

Technical difficulties which are encountered in the recovery of the 3-formylTHF product include the formation of hemiacetal oligomers and aldol condensation compounds from the hydroformylation products. The formation of these by-products is catalyzed by basic materials such as the phosphine, or even the phosphite, components of the hydroformylation catalyst, especially during the distillations at high pot temperatures. Recycling the catalyst system after removing the products by distillation or gas sparging is beset with the problem of removing these high-boiling by-products without damaging the catalyst. Usually, the high-boiling by-products continue to accumulate until the catalyst becomes blocked and loses activity. At that point, the only alternative is to discard the inactivated catalyst and start with a fresh catalyst charge. The formation and accumulation of the high-boiling by-products, aided by the base-catalyzed condensations, is why the initial aqueous extraction method of isolation/purification is preferred to other methods of product recovery.

In accordance with the present invention, 3-formylTHF is converted to 3-MeTHF by the hydrogenolysis of the formyl group to a methyl group while not affecting the tetrahydrofuran ring. The hydrogenolysis is carried out by contacting the 3-formylTHF with hydrogen in the presence of a catalyst system comprising (i) a catalytic amount of a Group VIII noble metal and (ii) a strong acid.

Palladium, platinum, ruthenium, rhenium and rhodium are examples of the metals which may be used in the process of the present invention. The form of the Group VIII noble metal or rhenium catalyst is not critical although the most efficient use of the catalytic metal is in a finely divided form on an appropriate support. Normally, supported, Group VIII noble metal or rhenium catalysts comprise about 0.1 to 25, preferably about 1 to 10, weight percent Group VIII noble or rhenium metal deposited on a suitable catalyst support material such as activated charcoal, carbon, silica, alumina, titania, zirconia, barium sulfate, calcium sulfate or zinc oxide. Alternatively, a Group VIII noble or rhenium metal in a finely divided form, e.g., palladium black, may be used even though it may not represent the most efficient use of the expensive noble metal. Also, salts such the chloride, fluoride, bromide, nitrate, carboxylates, e.g., acetate or benzoate; oxides; or hydroxide of Group VIII noble metals may be used. In addition to these soluble salts, insoluble salts such as the phosphates, sulfates, or iodides can be used. The catalyst preferably is selected from palladium and rhodium catalysts, especially supported catalysts comprising about 1 to 10 weight percent palladium deposited on charcoal or carbon.

The amount or concentration of the Group VIII noble metal or rhenium which is catalytically effective can be varied significantly depending upon the particular Group VIII noble metal used, the form in which it is used, the mode in which the process is operated and other process variables such as temperature, pressure and residence time. For example, the amount of Group VIII noble or rhenium metal present may be from 0.000001 to more than 100 gram atoms metal per mole of formyltetrahydrofuran present. However, when using certain modes of operation the amount of catalyst present per unit of reactant is virtually impossible to define. For example, the process may be operated continuously in a trickle bed manner wherein a liquid stream of formylTHF or a solution thereof is flowed (or "trickled") over a bed of catalyst in the presence of hydrogen under hydrogenolysis conditions of temperature and pressure to produce 3-MeTHF. In batch operation, the amount of Group VIII noble or rhenium metal present preferably is about 0.001 to 50, most preferably 0.1 to 10, gram atoms per mole of formyltetrahydrofuran present.

Examples of the strong acids which may be used in the second step of the process include sulfuric, phosphoric, nitric, hydrofluoric, hydrochloric, hydrobromic, hydriodic, or a sulfonic acid such as alkylsulfonic acids, arylsulfonic acids, e.g., toluenesulfonic acids, and polymeric sulfonic acids, e.g., acidic ion exchange resins comprising styrene/ divinylbenzene polymers bearing sulfo groups. The concentration of the monomeric strong acids may be in the range of 0.0001 molar to 5 molar although concentrations of 0.01 molar to 1 are preferred and concentrations of 0.05 to 0.5 molar are most preferred. When using the preferred amounts of palladium and strong acid, the mole ratio of palladium to strong acid is in the range of about 1:10 to 1:100. The present process preferably is operated in the presence of a strong acid in a concentration which gives the reaction mixture a pH of less than about 4, most preferably a pH in the range of about 0 to 2.

The use of hydriodic acid (HI) or a HI precursor such as iodine, metal iodide salts, organo-onium iodide compounds such as phosphonium iodides or ammonium iodides, or aromatic and, especially, alkyl and aralkyl iodides, as the strong acid in the process of this invention gives a larger conversion of the 3-formylTHF to 3-MeTHF than do other strong acids. However, the use of HI requires the presence of significantly larger amounts of the Group VIII noble metal. Furthermore, the use of conditions which favor conversion of a substantial amount, e.g., 80 mole percent or greater of 3-formylTHF to 3-MeTHF, also can result in significant decomposition of the tetrahydrofuran ring. Therefore, a preferred embodiment of the present invention entails a process for the coproduction of 3-MeTHF and 3-(hydroxymethyl)tetrahydrofuran (3-HOMeTHF), preferably by using a strong acid selected from sulfuric acid, phosphoric acid and nitric acid and the preferred reaction conditions which minimize decomposition of the tetrahydrofuran ring. In this preferred embodiment of my invention, the coproducts can be separated by conventional techniques and the 3-HOMeTHF can be recycled to the process along with fresh 3-formylTHF reactant. This preferred embodiment results in the best overall yield of the desired 3-MeTHF due primarily to minimizing decomposition of the tetrahydrofuran ring.

The process of the present invention may be carried out at a temperature in the range of about 80 to 280° C. and a hydrogen pressure of about 0.35 to 35 mPa (about 50 to 5000 psig). Preferred temperatures and hydrogen pressures are in the range of about 100 to 240° C. and about 1.4 to 7 mPa (about 200 to 1000 psig). The process may be performed in the presence of an extraneous, inert (nonreactive) solvent such as water or one or more aliphatic hydrocarbons. The concentrations of the 3-formylTHF in the inert solvent normally is about 0.01 to 5 molar or, more preferably, about 0.1 to 1 Molar. The process most preferably employs a water solution of 3-formylTHF formed in conjunction with an aqueous extraction of the 3-formylTHF product from the hydroformylation reaction mixture.

The reactant utilized in the hydrogenolysis process of this invention may include, in addition to 3-formylTHF, a minor or major amount of 3-HOMeTHF which is converted to 3-MeTHF. The 3-HOMeTHF may be coproduced as an intermediate hydrogenation product of the process of the present invention which is recovered and recycled to the process. Alternatively, the 3-HOMeTHF may be produced by contacting 3-formylTHF with hydrogen according to processes not within the scope of the present invention. Such processes are illustrated in certain of the comparative examples set forth herein.

The process of the present invention is further illustrated by the following examples. The following reference examples describe hydroformylation procedures for the production of the 3-formylTHF which is employed in the process of the invention. As used herein, the percent conversion of a reactant is:

$$\frac{\text{Moles Reactant Converted}}{\text{Moles Reactant Fed}} \times 100$$

and the percent selectivity to a particular compound:

$$\frac{\text{Moles Reactant Converted to the Compound}}{\text{Moles Reactant Converted}} \times 100$$

REFERENCE EXAMPLE 1

To a 300 mL, stainless steel autoclave was charged 150 mL of 2,5-DHF (d=0.927, 139 g, 1.93 moles), 37.6 mg of dicarbonyl rhodium (I) acetylacetonate (0.147 millimoles—mmol), and 95.4 mg of triphenylphosphine (0.364 mmol). The phosphorous to rhodium atomic ratio was 2.50 and the concentration of rhodium was 100 ppm (w/v). The autoclave was sealed and the run began by charging the system with 2.17 mPa (300 psig) of synthesis gas (hydrogen to carbon monoxide ratio=1.01:1) and rapidly stirring and heating the autoclave contents to 70° C. During the course of the reaction, the synthesis gas pressure was maintained at 2.17 mPa (300 psig) by periodic recharges of synthesis gas from a reservoir. Over 42 hours, the synthesis gas pressure drop amounted to a total of 45.95 mPa (6650 psig) and, at the end of this time, the uptake had nearly stopped.

Gas chromatographic (GC) analysis of a sample of the reaction product mixture showed a starting material conversion of 95.4%, a selectivity to 3-formylTHF of 94.7% and a selectivity to 2-formylTHF of 2.2%. Distillation of this product gave a material boiling at 83.5–85.5° C./12 mm Hg or 74.0–75.5° C./7 mm Hg which GC analysis showed was 98.9% pure 3-formylTHF. During the course of this fractional distillation, the base temperature reached a maximum of 127° C. and the product recovery was only 54%. Gas chromatographic analysis of the distillation pot residue after completion of the distillation showed a multitude of oligomeric by-products caused, presumably, by the phosphine-aided aldol condensation of the aldehydes in the product.

REFERENCE EXAMPLE 2

Reference Example 1 was repeated except the synthesis gas pressure was 4.58 mPa (650 psig). The time required to achieve 95% conversion of the starting material as measured by GC analysis was 43.5 hours. The selectivities and ratio of 3-formylTHF to 2-formylTHF were essentially the same as in Example 1.

REFERENCE EXAMPLE 3

Reference Example 1 was repeated except that the synthesis gas pressure was 0.79 mPa (100 psig). The time required to achieve 95% conversion of the starting material as measured by GC was 38.5 hours. The selectivities and ratio of 3-formylTHF to 2-formylTHF was essentially the same as in experiment 1.

REFERENCE EXAMPLE 4

Example 1 was repeated except that the phosphorous to rhodium atomic ratio was 12:1. The time required to achieve 95% conversion of the starting material was 36.5 hours. The selectivity to 3-formylTHF was 92.7% and the selectivity to 2-formylTHF was 7.1%.

REFERENCE EXAMPLE 5

Reference Example 4 was repeated except that the 2,5-DHF was dissolved in an 150 mL of toluene. The time required to achieve 95% conversion of the 2,5-DHF was 29.0 hours. The selectivity to 3-formylTHF was 91.9% and the selectivity to 2-formylTHF was 7.9%.

REFERENCE EXAMPLE 6

Reference Example 5 was repeated except the triphenylphosphine was replaced with tricyclohexylphosphine. The time required to achieve 95% conversion of the 2,5-DHF was 26.5 hours. GC analysis of the product at this point showed a 91.0% selectivity to 3-formylTHF and a 8.2% selectivity to 2-formylTHF.

REFERENCE EXAMPLE 7

Reference Example 5 was repeated except the triphenylphosphine catalyst component was replaced with an equimolar quantity of trimethylphosphite. The time required to achieve 95% conversion of the 2,5-DHF was 44.0 hours. GC analysis of the product showed an 89.2% selectivity to 3-formylTHF and a 9.1% selectivity to 2-formylTHF.

REFERENCE EXAMPLE 8

Reference Example 5 was repeated except the ratio of the hydrogen to the carbon monoxide in the synthesis gas was maintained at 2:1 rather than 1:1. The time required to achieve 95% conversion of the 2,5-DHF was 19.5 hours. GC of the product showed a 65.8% selectivity to 3-formylTHF, a 25.0% selectivity to 2-formylTHF, and a 9.0% selectivity to tetrahydrofuran.

REFERENCE EXAMPLE 9

Reference Example 5 was repeated except the rhodium source was changed to rhodium (II) 2-ethylhexanoate at a rhodium concentration of 100 ppm. The time required to achieve 95% conversion of the 2,5-DHF was 38.5 hours. The selectivity to 3-formylTHF was 94.0% and the selectivity to 2-formylTHF was 3.7%.

REFERENCE EXAMPLE 10

Reference Example 9 was repeated except that the rhodium concentration was 200 ppm and the amount of triphenylphosphine was increased to maintain a phosphorous to rhodium atomic ratio of 12:1. The time required to achieve 95% conversion of the 2,5-DHF starting material was 18.5 hours. The selectivity to 3-formylTHF was 94.1% and the selectivity to 2-formylTHF was 2.8%.

REFERENCE EXAMPLE 11

Reference Example 9 was repeated except that the rhodium concentration was 400 ppm and the amount of triphenylphosphine was increased to maintain a phosphorous to rhodium atomic ratio of 12:1. The time required to achieve 95% conversion of the 2,5-DHF reactant was 12.5 hours. The selectivity to 3-formylTHF was 95.3% and the selectivity to 2-formylTHF was 1.8%.

EXAMPLE 1

To a 300 mL stainless steel autoclave was charged 20 mL of 3-formylTHF (d=1.084, 21.7 g, 0.250 moles), 100 mL of water, 5.00 g of 5% palladium on activated charcoal, and 1.01 g of iodine (4.01 mmol). The autoclave was sealed and the experiment began by rapidly stirring and heating the autoclave contents to 175° C. under a hydrogen pressure of 3.55 mPa (500 psig) which was maintained by periodic additions of hydrogen. After one hour at 175° C., the pressure drop amounted to 3.76 mPa (530 psig). GC analysis of the contents showed the following selectivities: 71.4% to 3-MeTHF, 8.4% to 3-HOMeTHF, 2.0% to isopentane, 2.1% to isopentanol, 3.6% to 3-MeTHF dimers, and 12.5% to a multiplicity of minute amounts of unidentified compounds.

EXAMPLE 2

Example 1 was repeated except that the iodine was replaced with 1.1 mL of hydriodic acid (57% HI, d=1.701, 1.07 g HI, 8.34 mmol). All other conditions were identical. The selectivity to 3-MeTHF was 69.7% and the selectivity to 3-HOMeTHF was 7.1%.

EXAMPLE 3

Example 1 was repeated except that the iodine was replaced with 1.0 mL of concentrated sulfuric acid (98% $H_2SO_4$, d=1.878, 1.9 g $H_2SO_4$, 19.1 mmol). All other conditions were identical. The selectivity to 3-MeTHF was 14.6% and the selectivity to 3-HOMeTHF was 77.9%.

EXAMPLE 4

Example 1 was repeated except that the iodine was replaced with 1.0 mL of concentrated orthophosphoric acid (85 percent $H_3PO_4$, d=1.696, 1.44 g, 14.7 mmol) and the 5 percent palladium on activated charcoal was replaced with 10 weight percent palladium on activated charcoal. After stirring for 1 hour at 200° C., GC analysis showed a 3-formylTHF conversion of 99.7% and the following selectivities: 34.2% to 3-MeTHF, 56.5% to 3-(HOMe)THF, 1.8% to tetrahydrofuran, 0.4% to isopentanol, 0.6% to isopentane, and 6.5% to other materials.

COMPARATIVE EXAMPLE 1

Example 1 was repeated except the catalyst was 5 weight percent palladium on an acidic alumina support (no iodine or iodine compound was used) and the diluent was heptane instead of water. After stirring for 1 hour at 300° C., GC analysis showed a 3-formylTHF conversion of 99.6% and the following selectivities: 41.1% to 3-MeTHF, 19.4% to 3-HOMeTHF, 13.2% to tetrahydrofuran, 3.8% to isopentane, 1.1% to isopentanol, and 21.4% to other materials.

COMPARATIVE EXAMPLE 2

Comparative Example 1 was repeated except the catalyst was 20.4 g of 3.2 mm (⅛ inch) diameter copper chromite pellets and the iodine was omitted. After circulating the reaction mixture for 2 hours over a bed of the catalyst at 330° C., GC analysis showed a 3-formylTHF conversion of 99.9% with the following selectivities: 41.3% to 3-MeTHF, 5.9% to 3-(HOMe)-THF, 17.7% to tetrahydrofuran, 5.8% to isopentanol, 0.8% to isopentane, and 28.5% to other materials.

COMPARATIVE EXAMPLE 3

Comparative Example 1 was repeated except the catalyst was 24.6 g of 50 weight percent nickel on silica/alumina and the iodine was omitted. After circulating the reaction mixture for 1 hour over a bed of this catalyst at 150° C., GC analysis showed a 3-formylTHF starting material conversion of 84.2% with the following selectivities: 0.2% to 3-MeTHF, 95.1% to 3-HOMeTHF, 0.2% to tetrahydrofuran, 0.1% to isopentanol, and 4.4% to other materials.

COMPARATIVE EXAMPLE 4

Comparative Example 2 was repeated except that all acidic materials were excluded from the catalyst system and the water was replaced with 100 mL of anhydrous methanol. After stirring for 2 hours at 175° C., GC analysis showed a 99.8% conversion of the 3-formylTHF with the selectivities: 0.1 % to 3-MeTHF, 99.1% to 3-HOMeTHF, 0.1% to tetrahydrofuran, 0.1% to isobutanol, and 0.6% to other compounds.

COMPARATIVE EXAMPLE 5

Example 1 was repeated except the iodine was replaced with 1.0 mL of trifluoroacetic acid (d=1.480, 1.5 g, 13 mmol). After stirring for 1 hour at 150° C., GC analysis showed a starting material conversion of 99.8% with the following selectivities: 1.4% to 3-MeTHF, 94.5% to 3-HOMeTHF, 1.4% to tetrahydrofuran, 0.5% to isopentane, and 2.2% to other materials.

COMPARATIVE EXAMPLE 6

Comparative Example 1 was repeated except the catalyst was 2.48 grams of 10 weight percent palladium on activated charcoal and the catalyst promoter was 1.0 mL of trifluoroacetic anhydride (d=1.487, 1.5 g, 7.1 mmol). After stirring for 1 hour at 290° C., GC analysis showed that 99.9% of the 3-formylTHF reactant had been converted with the following product selectivities: 35.2% to 3-MeTHF, 12.3% to 3-HOMeTHF, 18.0% to tetrahydrofuran, 0.7% to isopentanol, 0.6% to isopentane, and 31.2% to other compounds.

The invention has been described in detail with particular reference to preferred embodiments thereof, but it will be understood that variations and modifications can be effected within the spirit and scope of the invention.

I claim:

1. Process for the preparation of 3-methyltetrahydrofuran which comprises contacting 3-formyltetrahydrofuran with hydrogen in the presence of a catalyst system comprising a Group VIII nobel metal or rhenium and a strong acid under hydrogenolysis conditions of temperature and pressure to produce 3-methyltetrahydrofuran.

2. Process according to claim 1 wherein the Group VIII noble metal is palladium and the hydrogenation conditions of temperature and pressure comprise temperatures in the range of about 100 to 240° C. and hydrogen pressures in the range of about 1.4 to 7 mpa.

3. Process according to claim 1 wherein the Group VIII nobel metal catalyst is a supported catalyst comprising about 1 to 10 weight percent palladium on charcoal or carbon, the strong acid is sulfuric acid, phosphoric acid or nitric acid and the process is carried out at a pH of less than about 4.

4. Process for the coproduction of 3-methyltetrahydrofuran and 3-(hydroxymethyl) tetrahydrofuran which comprises contacting 3-formyltetrahydrofuran with hydrogen in the presence of a catalyst system comprising a supported catalyst comprising about 1 to 10 weight percent palladium on charcoal or carbon and a strong acid selected from sulfuric acid, phosphoric acid and nitric acid, wherein the process is carried out at a pH of about 0 to 2 at a temperature in the range of about 100 to 240° C. and a hydrogen pressure of about 1.4 to 7 mPa.

5. Process according to claim 4 wherein water is present.

6. Process for the preparation of 3-methyltetrahydrofuran which comprises contacting 3-formyltetrahydrofuran with hydrogen in the presence of a catalyst system comprising a Group VIII nobel metal and iodine or an iodine compound under hydrogenolysis conditions of temperature and pressure to produce 3-methyltetrahydrofuran.

7. Process according to claim 6 wherein the Group VIII noble metal is palladium and the hydrogenolysis conditions of temperature and pressure comprise temperatures in the range of about 100 to 240° C. and hydrogen pressures in the range of about 1.4 to 7 mPa.

8. Process according to claim 7 wherein the iodine compound is hydrogen iodide.

* * * * *